United States Patent [19]
Larner et al.

[11] Patent Number: 6,093,697
[45] Date of Patent: *Jul. 25, 2000

[54] SYNTHETIC INSULIN MIMETIC SUBSTANCES

[75] Inventors: Joseph Larner, Charlottesville; John Price, Richmond; Thomas Piccariello, Blacksburg; Laura Huang, Charlottesville, all of Va.

[73] Assignee: The University of Virginia Patent Foundation, Charlottesville, Va.

[*] Notice: This patent is subject to a terminal disclaimer.

[21] Appl. No.: 08/902,338

[22] Filed: Jul. 29, 1997

Related U.S. Application Data

[63] Continuation-in-part of application No. 08/335,015, Nov. 7, 1994, Pat. No. 5,652,221.

[51] Int. Cl.[7] .......................... A61K 31/70; C07H 15/00
[52] U.S. Cl. .................. 514/35; 514/25; 514/53; 514/62; 514/866; 536/17.2
[58] Field of Search ................. 514/25, 35, 53, 514/62, 866; 536/17.2

[56] References Cited

U.S. PATENT DOCUMENTS

| | | | |
|---|---|---|---|
| 3,773,919 | 11/1973 | Boswell et al. | 424/19 |
| 4,446,064 | 5/1984 | Larner et al. | 530/344 |
| 4,485,045 | 11/1984 | Regen | 554/80 |
| 4,544,545 | 10/1985 | Ryan et al. | 424/1.1 |
| 5,652,221 | 7/1997 | Larner et al. | 514/35 |

FOREIGN PATENT DOCUMENTS

| | | |
|---|---|---|
| 0 036 676 | 9/1981 | European Pat. Off. . |
| 0 052 322 | 5/1982 | European Pat. Off. . |
| 0 058 481 | 8/1982 | European Pat. Off. . |
| 0 088 046 | 9/1983 | European Pat. Off. . |
| 0 102 324 | 3/1984 | European Pat. Off. . |
| 0 133 988 | 3/1985 | European Pat. Off. . |
| 0 142 641 | 5/1985 | European Pat. Off. . |
| 0 143 949 | 6/1985 | European Pat. Off. . |
| 0245956 | 11/1987 | European Pat. Off. . |
| 32 18 121 | 11/1983 | Germany . |
| 4-28412 | 5/1992 | Japan . |

OTHER PUBLICATIONS

Ellestad et al. *J. Antibiotics* 1982, 35(10), 1418–1421.
Mohlenkamp et al. *Aminoglycoside Antibiotics*, Aug. 1968, 33(8), 3163–3165.
Larner et al. *Biochem. Biophys. Res. Commun.* 1988, 151(3), 1416–1426.
Machicao et al. *Biochem. J.* 1990, 266, 909–916.
Berlin et al. *Tetrahedron* 1991, 47(1), 1–20.
Alenfalk, S. et al., "Syntheses of O–(2–Acetamido–2–deoxy-α–D–galactopyranosyl)–myo–inositols," *J. Carbohydrate Chem.* 10(6):937–946 (1991).
Berlin, W.K. et al., "Glycosyl–inositol Derivatives II. Synthesis of 2–Amino–2–deoxy–D–galactosyl–α–1,3–D–chiro–inositol," *Tetrahedron Lett.* 31(8):1109–1112 (1990).
Berlin, W.K. et al., "Glycosyl–inositol Derivatives III. Synthesis of Hexosamine–inositol–phosphates Related to Putative Insulin Mediators," *Tetrahedron* 47(1):1–20 (1991).
Cottaz, S. et al., "Parasite Glycoconjugates. Part 1. The Synthesis of Some Early and Related Intermediates in the Biosynthetic Pathway of Glycosyl–phosphatidylinositol Membrane Anchors," *J. Chem. Soc. Perkin Trans.* 1:2945–2951 (Dec. 1993).
Eppstein, D.A. et al., "Biological activity of liposome–encapsulated murine interferon γ is mediated by a cell membrane receptor," *Proc. Natl. Acad. Sci. USA* 82(11):3688–3692 (1985).

(List continued on next page.)

*Primary Examiner*—Kathleen K. Fonda
*Attorney, Agent, or Firm*—Sterne, Kessler, Goldstein & Fox P.L.L.C.

[57] ABSTRACT

Compounds are disclosed which have the formula (I)

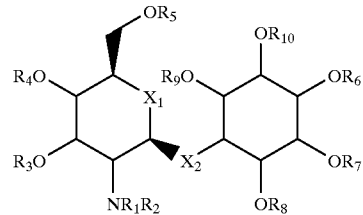

wherein $R_1$–$R_2$ are each independently selected from the group consisting of: (a) a hydrogen atom; and (b) a lower alkyl group, straight or branched chain, having 1 to 8 carbon atoms; or $R_1$–$R_2$ and the nitrogen atom to which they are bonded may together form a heterocyclic group; $R_3$–$R_{10}$ are each independently selected from the group consisting of: (a) a hydrogen atom; (b) an alkyl group, straight or branched chain, having 1 to 24 carbon atoms; (c) a cycloalkyl group having 3 to 10 carbon atoms; (d) an alkenyl group, straight or branched chain, having 2 to 24 carbon atoms; (e) a cycloalkenyl group having 4 to 10 carbon atoms and one or more non-adjacent double bonds; (f) an aryl group having 6 to 10 carbon atoms; (g) an aralkyl group having 7 to 34 carbons atoms; (h) a heteroaryl group having 4 to 9 carbon atoms and at least one heteroatom selected from the group consisting of oxygen, nitrogen and sulfur; (i) a carboxyalkyl group, straight or branched chain, having 2 to 24 carbon atoms; (j) a carboxyaryl group having 7 to 34 carbon atoms; and (k) a heterocyclic group having 2 to 9 carbon atoms and at least one heteroatom selected from the group consisting of oxygen, sulfur and nitrogen; or any adjacent two of $R_3$–$R_{10}$ may together form a cycloalkyl group or heterocyclic group; and $X_1$ and $X_2$ are each independently selected from the group consisting of an oxygen atom, a sulfur atom and a nitrogen atom. Pharmaceutical compositions containing these compounds and the use thereof for the treatment of disorders of glucose metabolism are also disclosed.

20 Claims, 7 Drawing Sheets

OTHER PUBLICATIONS

Hillmen, P. et al., "Specific defect in N–acetylglucosamine incorporation in the biosynthesis of the glycosylphosphatidylinositol anchor in cloned cell lines from patients with paroxysmal nocturnal hemoglobinuria," *Proc. Natl. Acad. Sci. USA* 90(11):5272–5276 (Jun. 1993).

Hwang, K.J. et al., "Hepatic uptake and degradation of unilamellar sphingomyelin/cholesterol liposomes: A kinetic study," *Proc. Natl. Acad. Sci. USA* 77(7):4030–4034 (1980).

Konradsson, P. et al., "Iodonium Promoted Reactions of Disarmed Thioglycosides," *Tetrahedron Lett.* 31(30):4313–4316 (1990).

Langer, R. et al., "Biocompatibility of polymeric delivery systems for macromolecules," *J. Biomed. Mater. Res.* 15(2):267–277 (1981).

Langer, R., "Controlled release of macromolecules," *Chemtech* 21(2):98–105 (1982).

Larner, J. et al., "Rat Liver Insulin Mediator Which Stimulates Pyruvate Dehydrogenase Phosphatase Contains Galactosamine and D–Chiroinositol," *Biochem. Biophys. Res. Commun.* 151(3):1416–1426 (Mar. 1988).

Lemonnier, M. et al., "Use of Chemical Ionization in Gas Chromatographic/Mass Spectrometric Screening of Human Urine for Disaccharides containing Inositol," *Biomed. Mass Spectrom.* 12(3):100–105 (1985).

Ley, S.V. and Yeung, L.L., "Microbial Oxidation in Synthesis: Preparation of a Potential Insulin Mimic from Benzene," *Synlett* 12:997–998 (1992).

Maehr, H. et al., "Microbial Products. IV. X–14847, A New Aminoglycoside from *Micromonospora echinospora*," *J. Antibiotics XXXIII* (12):1431–1436 (1980).

Menon, A.K. et al., "Cell–free Synthesis of Glycosyl–phosphatidylinositol Precursors for the Glycolipid Membrane Anchor of *Trypanosoma brucei* Variant Surface Glycoproteins. Structural Characterization of Putative Biosynthetic Intermediates," *J. Biol. Chem.* 265(16):9033–9042 (Jun. 1990).

Meyer, D.M. et al., "Isolation and characterization of 1–O–α–2–acetamido–2–deoxy–D–galactopyranosyl–myo–inositol from pregnancy urine," *FEBS Lett.* 172(1):99–102 (Jun. 1984).

Mootoo, D.R. et al., "n–Pentenyl Glycosides Facilitate a Stereoselective Synthesis of the Pentasaccharide Core of the Protein Membrane Anchor Found in *Trypanosoma brucei*," *J. Am. Chem. Soc.* 111(22):8540–8542 (1989).

Nishihara, M. et al., "Archaea Contain a Novel Diether Phosphoglycolipid with a Polar Head Group Identical to the Conserved Core of Eucaryal Glycosyl Phosphatidylinositol," *J. Biol. Chem.* 267(18):12432–12435 (Jun. 1992).

Ogita, T. et al., "The Structure of Adenomycin ($C_{19-97}$ Substance)," *Tetrahedron Lett.* 21(33):3203–3206 (1980).

Plourde, R. and d'Alarcao, M., "Synthesis of a Potentially Insulin–mimetic Phosphodisaccharide," *Tetrahedron Lett.* 31(19):2693–2696 (1990).

Plourde, R. et al., "Synthesis and Characterization of an Insulin–Mimetic Disaccharide," *J. Org. Chem.* 57(9):2606–2610 (1992).

Reddy, K.K. et al., "Insulin Second Messengers: Synthesis of 6–0–(2–Amino–2–deoxy–α–D–glucopyranosyl)–D–chiro–inositol–1–phosphate," *Tetrahedron Lett.* 34(49): 7869–7872 (Dec. 1993).

Saltiel, A.R. and Cuatrecasas, P., "Insulin stimulates the generation from hepatic plasma membranes of modulators derived from an inositol glycolipid," *Proc. Natl. Acad. Sci. USA* 83(16):5793–5797 (1986).

Saltiel, A.R., "Second Messengers of Insulin Action," *Diabetes Care* 13(3):244–256 (Mar. 1990).

Sidman, K.R. et al., "Controlled Release of Macromolecules and Pharmaceuticals from Synthetic Polypeptides Based on Glutamic Acid," *Biopolymers* 22(1):547–556 (1983).

Udodong, U.E. et al., "A Ready, Convergent Synthesis of the Heptasaccharide GPI Membrane Anchor of Rat Brain Thy–1 Glycoprotein," *J. Am. Chem. Soc.* 115(17):7886–7887 (Aug. 1993).

English Language Abstract of EP 0 052 322 (Document AM1), Dialog File 351 (Derwent World Patents Index), Acc. No. 3496164, May 1982.

English Language Abstract of EP 0 088 046 (Document A01), Dialog File 351 (Derwent World Patents Index), Acc. No. 3764179, Sep. 1983.

English Language Abstract of DE 32 18 121 (Document AP1), Dialog File 351 (Derwent World Patents Index), Acc. No. 3825303, Nov. 1983.

English Language Abstract of EP 0 102 324 (Document AL2), Dialog File 351 (Derwent World Patents Index), Acc. No. 3918746, Mar. 1984.

English Language Abstract of EP 0 133 988 (Document AM2), Dialog File 351 (Derwent World Patents Index), Acc. No. 4236631, Mar. 1985.

English Language Abstracts of EP 0 142 641 (Document AN2), Dialog File 351 (Derwent World Patents Index), Acc. No. 4295804 and Acc. No. 4266799, May 1985.

English Language Abstract of JP 4–28412 (Document AP2), Dialog File 351 (Derwent World Patents Index), Acc. No. 4225352, May 1992.

SCHEME 1

SCHEME 6

FIG.6

SCHEME 7

FIG.7

SYNTHETIC INSULIN MIMETIC SUBSTANCES

This application is a continuation-in-part of prior application Ser. No. 08/335,015, filed Nov. 7, 1994 and now U.S. Pat. No. 5,652,221.

FIELD OF THE INVENTION

This invention relates to compounds of the formula (I)

(I)

and pharmaceutical compositions containing them. These compounds mimic the action of insulin and are useful for the treatment of disorders of glucose metabolism, such as impaired glucose tolerance, elevated blood glucose associated with type II diabetes and insulin resistance.

BACKGROUND OF THE INVENTION

It has long been known that the cellular metabolic actions of insulin involve the generation of a low molecular weight substance that mimics certain actions of insulin. See Larner et al., U.S. Pat. No. 4,446,064. An inositol glycan structure was first proposed for an insulin mediator in 1986. See Saltiel et al., *Proc. Nat. Acad. Sci.* 83:5793–97 (1986). Since these initial studies, structural variations in the insulin mediator have been reported in a number of laboratories. See Saltiel, Second Messengers of Insulin Action, *Diabetes Care*, 133:244–256 (1990). Specifically, analyses from the laboratory of Larner demonstrated the presence of significant amounts of D-chiro-inositol and galactosamine as features of the inositol glycan structure. Larner et al., *Biochem. Biophys. Res. Comm.* 151:1416–26 (1988). Despite progress in identifying the structure and biogenesis of inositol glycans released from the plasma membrane in response to insulin, identification of the precise biological utility of these compounds will depend upon the precise structural identification and examination of their insulin mimetic properties.

The identification of substances that mediate or mimic the action of insulin could lead to the development of novel structures which may be of clinical use in the treatment of persons having disorders of glucose metabolism, such as impaired glucose tolerance, elevated blood glucose associated with Type II diabetes, and insulin resistance and physiological conditions associated therewith. Physiological conditions known in the art to be associated with insulin resistance include: diabetes mellitus and its chronic complications; obesity; hyperlipidemia and dyslipidemia; atherosclerosis; hypertension; cardiovascular disease; AIDS; cancer; wasting/cachexia; sepsis; trauma associated with burns, malnutrition and/or stress; aging; lupus and other autoimmune diseases; endocrine disease; hyperuricemia; polycystic ovary syndrome; and complications arising from athletic activity or inactivity.

Insulin mimetic molecules extracted from biological sources present a variety of undesirable characteristics, including possible contamination as well as unreliable or limited sources of supply of naturally occurring molecules. It is therefore desirable to devise a synthetic molecule which mimics the activity of insulin or its mediators and which can be synthesized without resort to extracts from animal tissue.

SUMMARY OF THE INVENTION

It has been found that certain small amino disaccharides can mimic the action of insulin and act to reduce elevated blood glucose levels. A first embodiment of the present invention is therefore directed to compounds of the formula (I)

(I)

wherein $R_1-R_{10}$ and $X_1-X_2$ are defined below, and derivatives and metabolites thereof. Examples of the amino disaccharides of the present invention include molecules consisting of galactosamine and isomers and derivatives of inositol, such as 2-deoxy-2-amino-galactopyranosyl pinitol and derivatives of these amino disaccharides.

A second embodiment of the present invention is directed to pharmaceutical compositions containing the inventive compounds. These pharmaceutical compositions are useful for treating disorders of glucose metabolism, such as impaired glucose tolerance, elevated blood glucose associated with Type II diabetes, and insulin resistance and physiological conditions associated therewith.

It is to be understood that both the foregoing general description and the following detailed description are exemplary and explanatory only and are intended to provide further explanation of the invention as claimed.

DETAILED DESCRIPTION OF THE PREFERRED EMBODIMENTS

In a first preferred embodiment, the present invention is directed to compounds of the formula (I)

(I)

wherein $R_1-R_2$ are each independently selected from the group consisting of:

(a) a hydrogen atom; and (b) a lower alkyl group, straight or branched chain, having 1 to 8 carbon atoms, such as methyl, ethyl and propyl; or $R_1$–$R_2$ and the nitrogen atom to which they are bonded may together form a heterocyclic group;

$R_3$–$R_{10}$ are each independently selected from the group consisting of:

(a) a hydrogen atom;

(b) an alkyl group, straight or branched chain, having 1 to 24 carbon atoms, such as methyl, ethyl, propyl, t-butyl, pentyl, octyl and dodecyl;

(c) a cycloalkyl group having 3 to 10 carbon atoms, such as cyclopropyl, cyclopentyl and cyclohexyl;

(d) an alkenyl group, straight or branched chain, having 2 to 24 carbon atoms;

(e) a cycloalkenyl group having 4 to 10 carbon atoms and one or more non-adjacent double bonds, such as cyclopentenyl and cyclopentadienyl;

(f) an aryl group having 6 to 10 carbon atoms, such as phenyl and naphthyl;

(g) an aralkyl group having 7 to 34 carbons atoms, such as benzyl and 2-phenylethyl;

(h) a heteroaryl group having 4 to 9 carbon atoms and at least one heteroatom selected from the group consisting of oxygen, nitrogen and sulfur, such as furyl, pyridyl and thienyl;

(i) a carboxyalkyl group, straight or branched chain, having 2 to 24 carbon atoms, such as acetyl;

(j) a carboxyaryl group having 7 to 34 carbon atoms, such as benzoyl; and (k) a heterocyclic group having 2 to 9 carbon atoms and at least one heteroatom selected from the group consisting of oxygen, sulfur and nitrogen; or any adjacent two of $R_3$–$R_{10}$ may together form a cycloalkyl group or heterocyclic group;

and

$X_1$ and $X_2$ are each independently selected from the group consisting of an oxygen atom, a sulfur atom and a nitrogen atom.

Alkoxy (b), aryloxy (f), and ester (i-j) substituents are useful in protecting the molecule, modifying its hydrophilicity and/or modulating its insulin mimetic properties and so are particularly preferred substituents.

Preferably, $R_1$ and $R_2$ are each a hydrogen atom or a lower alkyl group having from 1 to 4 carbon atoms, such as methyl or ethyl. More preferably, $R_1$ and $R_2$ are each a hydrogen atom.

Preferably, $X_1$ and $X_2$ are each an oxygen atom. More preferably, when $X_1$ and $X_2$ are each an oxygen atom, the hexosamine component of the inventive compounds is selected from the group consisting of 2-deoxy-2-amino-β-D-galactose and 2-deoxy-2-amino-β-D-glucose. Most preferably, the hexosamine component is 2-deoxy-2-amino-β-D-galactose.

Preferably, the inositol component of the inventive compounds is selected from the group consisting of myo-inositol and chiro-inositol. More preferably, the inositol component is chiro-inositol, i.e., compounds of the formula (II)

(II)

wherein $R_1$–$R_{10}$ and $X_1$ and $X_2$ are as defined above.

Preferably, for compounds of the formula (II), at least one of $R_3$–$R_8$ is selected from the group consisting of an alkyl group, a cycloalkyl group, an aryl group, an aralkyl group, a carboxyalkyl group, or a carboxyaryl group. More preferably, at least one of $R_3$–$R_8$ is an alkyl group. Most preferably, $R_8$ is a methyl group.

The compounds of the present invention may be prepared according to any of the methods known to those skilled in the art. For example, the compounds of this invention can be prepared in the following manner.

Figure 1:
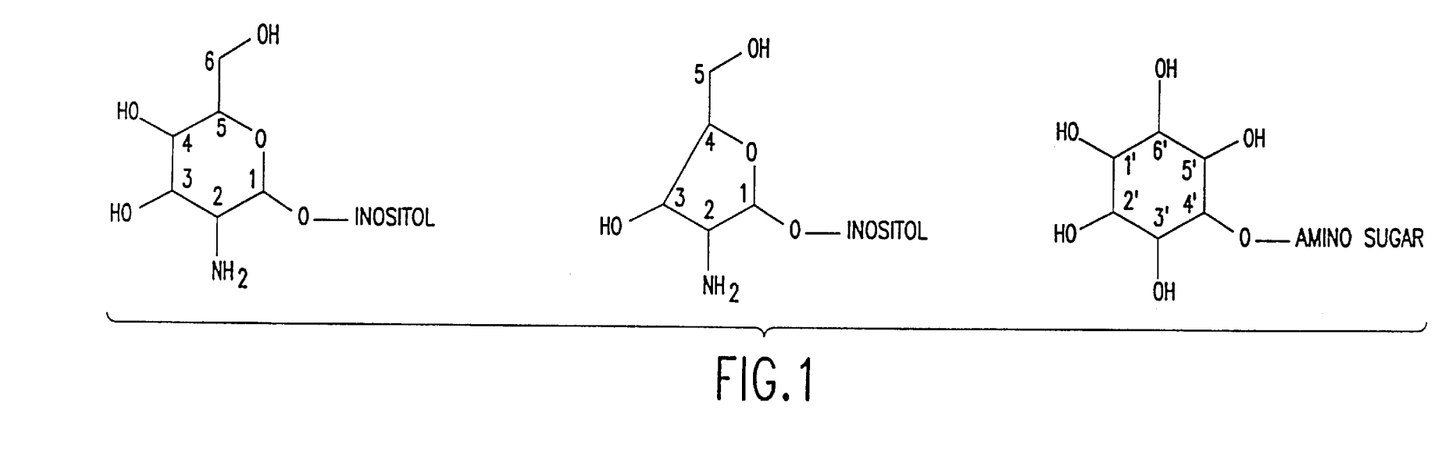
FIG. 1 is an illustration of the numbering system used to describe compounds of the present invention.
Figure 2:
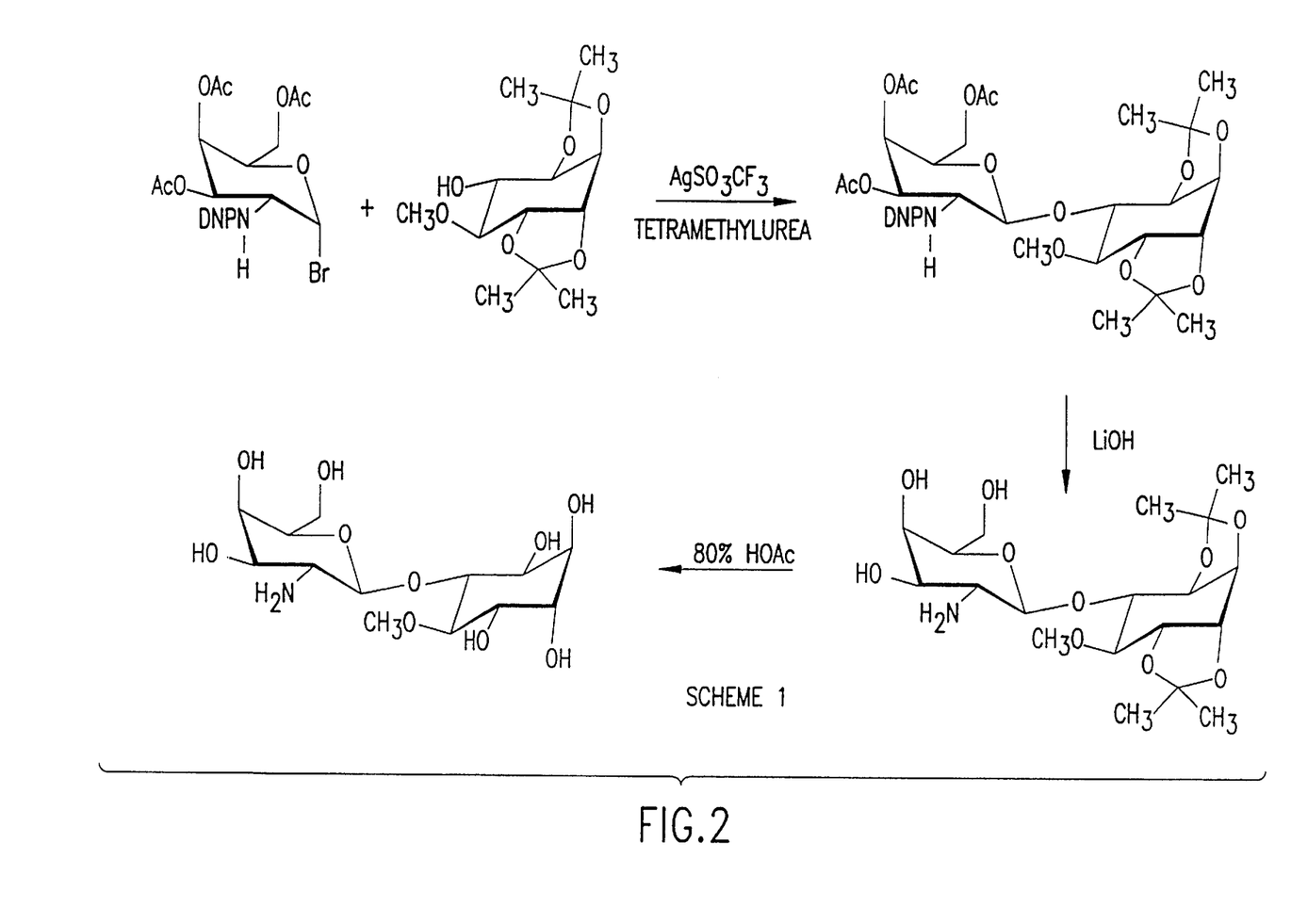
FIGS. 2 through 7 illustrate exemplary synthetic pathways used to prepare compounds of the present invention.

The beta-glycosides of 2-deoxy-2-amino sugars with derivatives of inositol of this invention are prepared by the reaction of an appropriately protected amino sugar precursor having a leaving group at the 1-position (glycosyl donor) with a free hydroxyl group of a suitably protected inositol (glycosyl acceptor) in the presence of a promoter, followed by deprotection. For example, 4'-O-(2-deoxy-2-amino-β-D-galactopyranosyl)-D-pinitol is prepared by the glycosylation/deprotection sequence shown in Scheme 1, which is set forth in FIG. 2.

Figure 3:
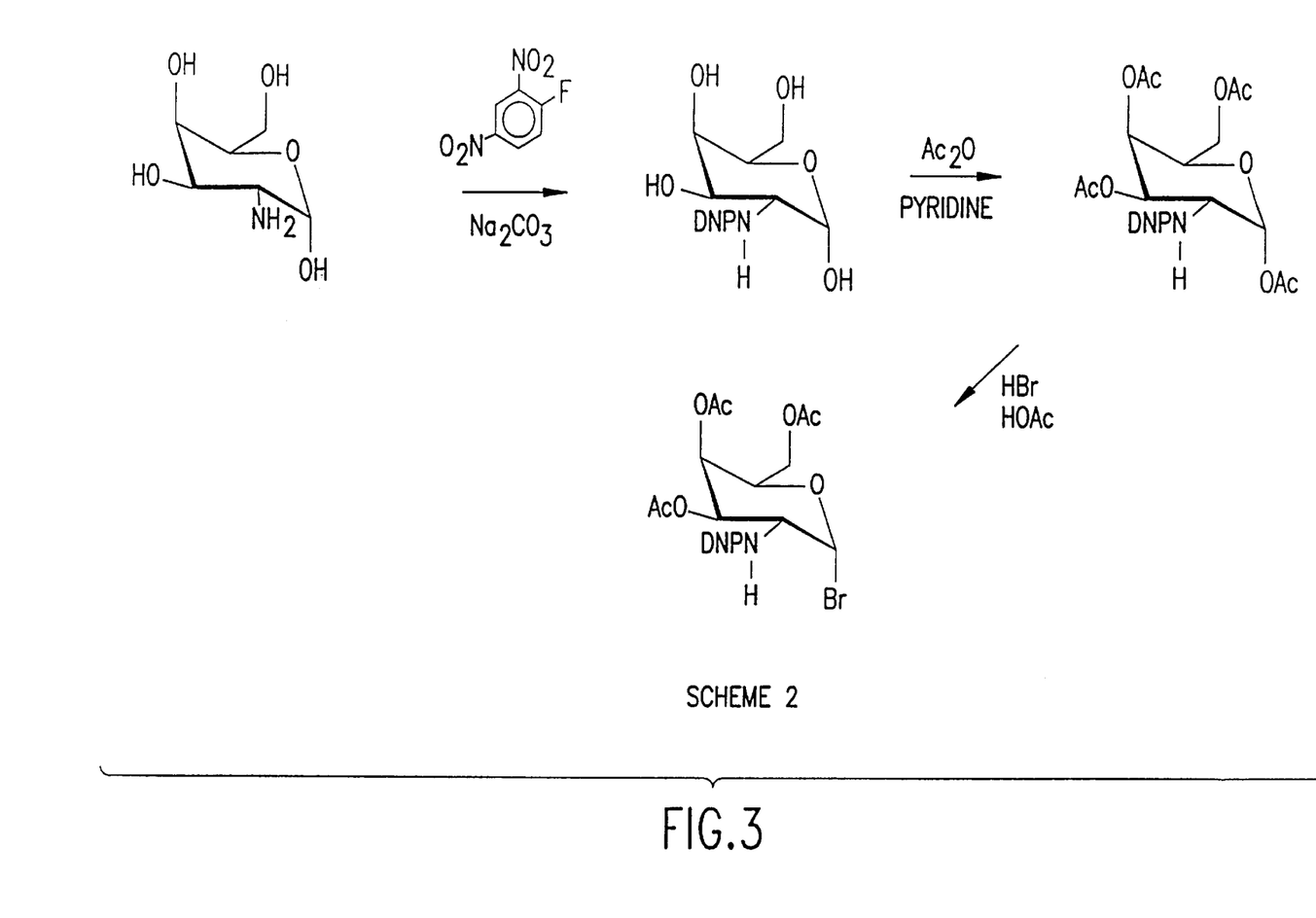

The glycosyl donor, 1-bromo-1,2-dideoxy-3,4,6-tri-O-acetyl-2-dinitro-phenylaminogalactose, is prepared as shown in Scheme 2, which is set forth in FIG. 3, and described in detail below.

Figure 4:
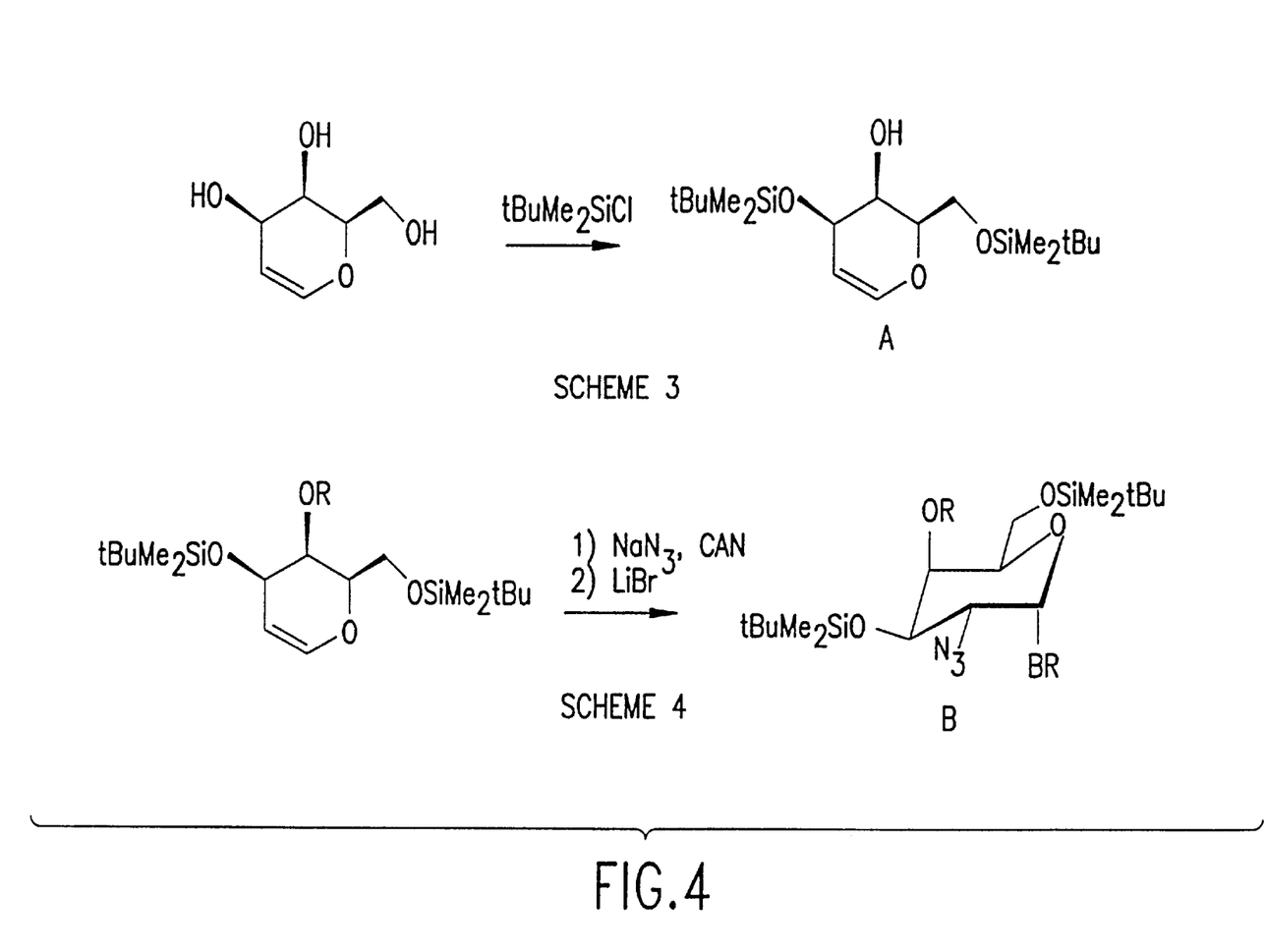

Other glycosyl donors are prepared by straight forward synthetic manipulation of available precursors. For instance, selective derivatization of the 4-position of galactal can be achieved by treating the compound with 2 equivalents of t-butyldimethylsilyl chloride as shown in Scheme 3, which is set forth in FIG. 4. Compound A can be easily converted to an ether or ester by known Williamson or Schotten-Bauman techniques. Azidonitration and bromide displacement on B provides a glycosyl donor which, following reaction with a glycosyl acceptor in the presence of silver silicate, reduction of the azido group by hydrogenation and deprotection with fluoride, yields a beta-glycoside of 2-deoxy-2-aminogalactose substituted at the 4-position with an ether or an ester.

Figure 5:
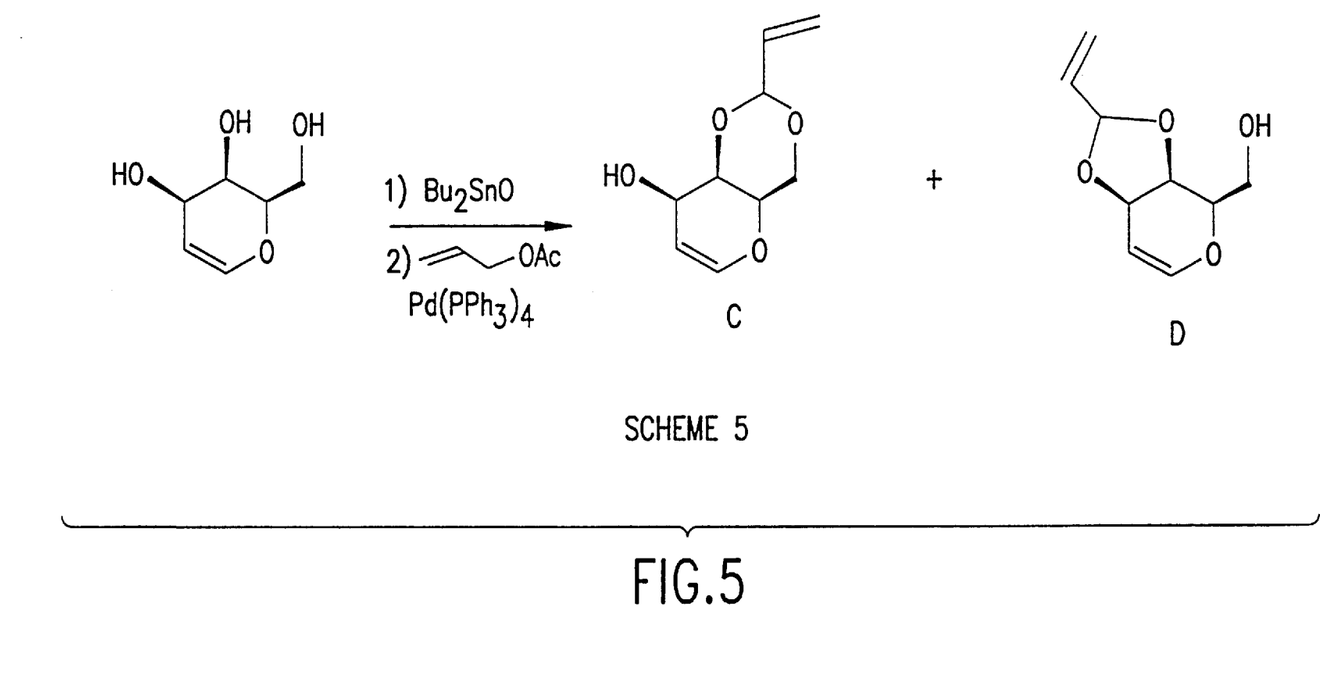

Similarly, as is shown in scheme 5 which is set forth in FIG. 5, compounds C and D can be easily separated and converted into beta-glycosides of 2-deoxy-2-aminogalactose substituted at the 3 or 6-position with an ether or an ester.

Figure 6:
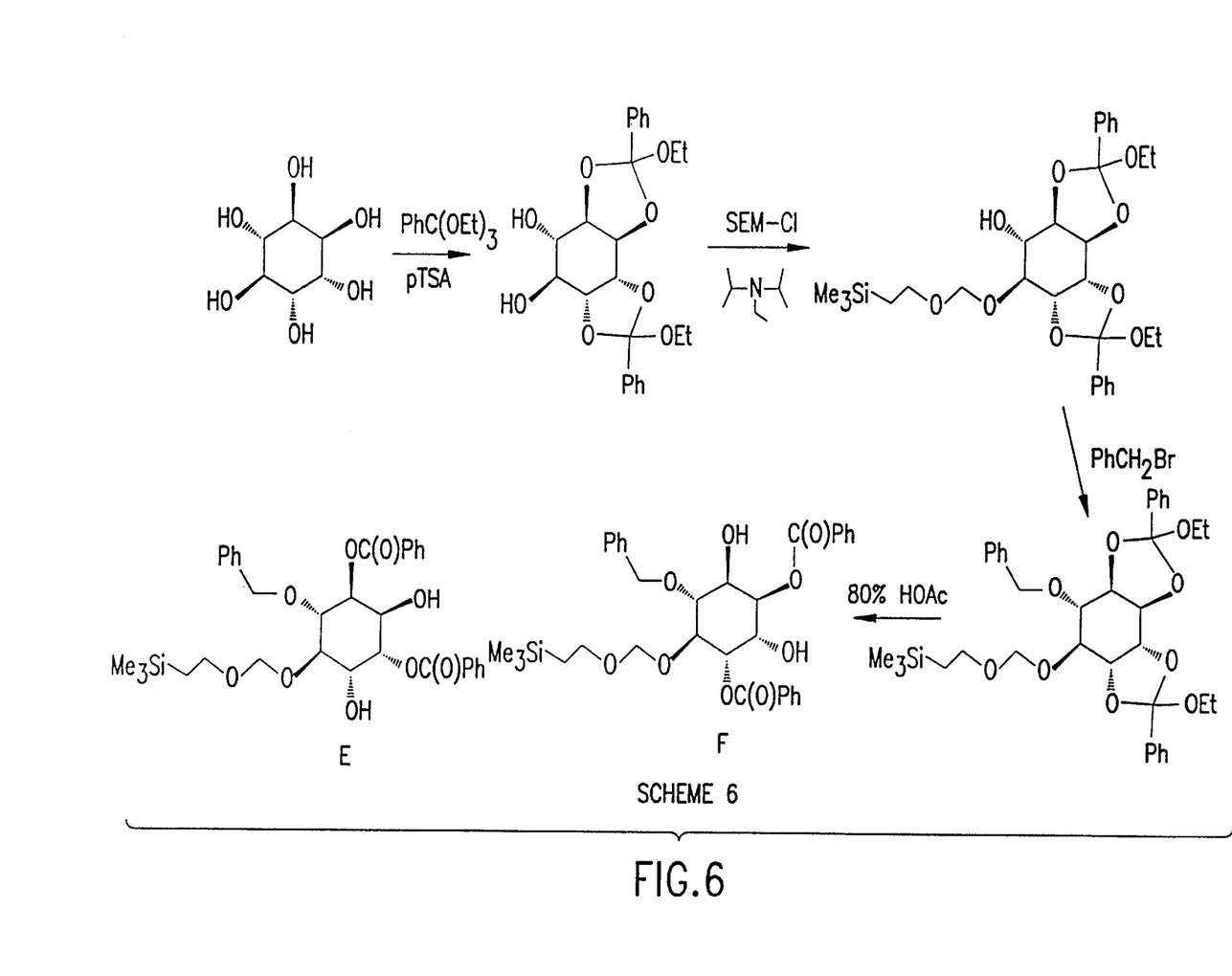
Figure 7:
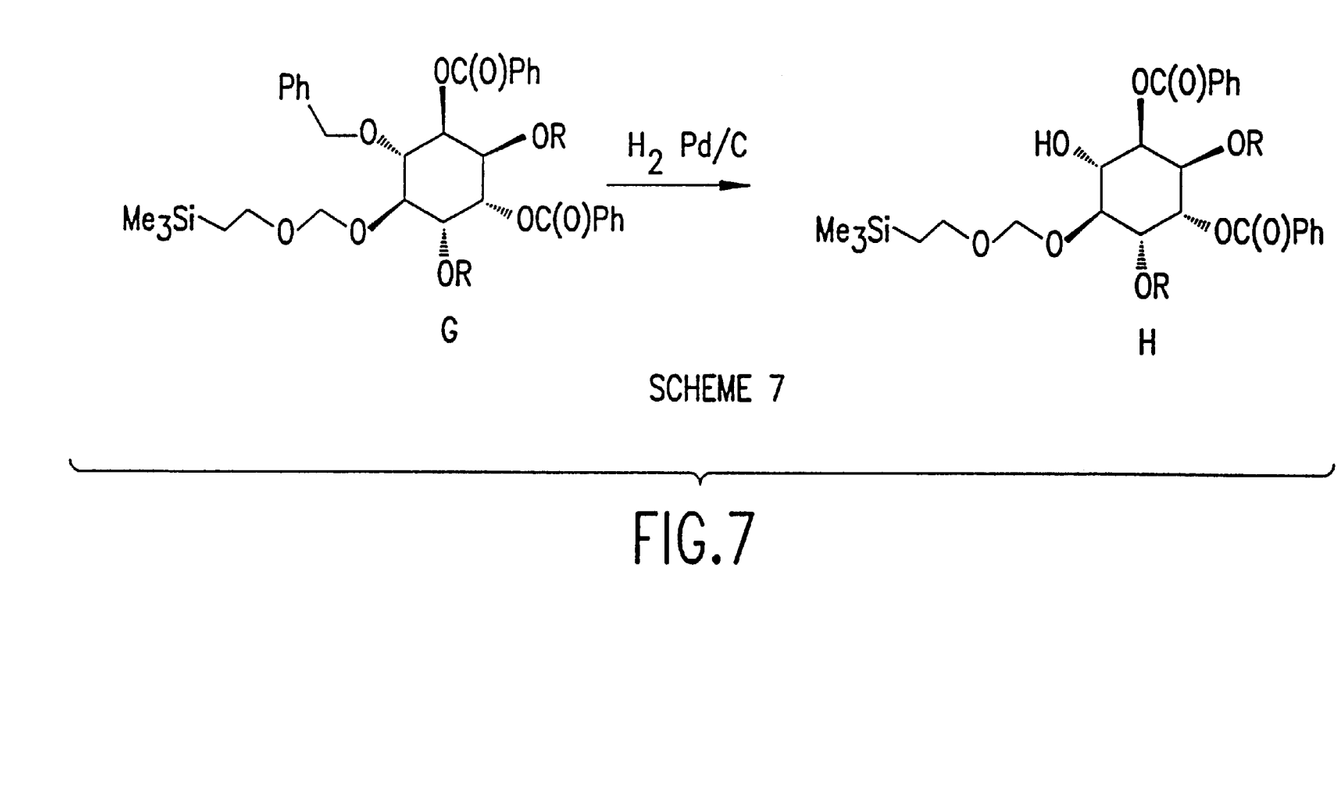

The glycosyl acceptor, 1',2'; 5',6'-di-O-isopropylidene-D-pinitol, used in the synthesis of 4'-O-(2-deoxy-2-amino-β-D-galacopyranosyl)-D-pinitol as in Scheme 1 was prepared by the reaction of D-pinitol with dimethoxypropane in the presence of a catalytic amount of p-toluenesulfonic acid. Other glycosyl acceptors can be prepared readily. For instance, compounds E and F, which can be prepared as shown in Scheme 6, which is set forth in FIG. 6, can be mono or dialklated regioselectivly using Williamson techniques. Glycosides containing chiro-inositols with alkoxy substituents at the 2 and 6 positions can be obtained by catalytic debenzylation of G to give glycosyl acceptor H as set forth in FIG. 7, followed by glycosylation of H and deprotection using standard techniques. Similarly, glycosides containing chiro-inositols with alkoxy substituents at the 1 and 5-positions can be prepared from G.

It will be appreciated that conditions caused by a decrease in the standard or normal level of insulin activity in an individual, can be treated by administration of one or more of the inventive insulin mimetic compounds or a derivative or metabolite thereof. A second preferred embodiment of the present invention is therefore directed to pharmaceutical compositions containing the inventive compounds described above.

The pharmaceutical compositions of the present invention will be formulated and dosed in a fashion consistent with good medical practice, taking into account the clinical condition of the individual patient (especially the side effects of treatment with the inventive compounds alone), the site of delivery of the pharmaceutical composition, the method of administration, the scheduling of administration, and other factors known to practitioners. The "effective amount" of a compound of the present invention for pharmaceutical purposes is thus determined by such considerations.

As a general proposition, the total pharmaceutically effective amount of a disaccharide of the present invention administered per dose will be in the range of about 10 $\mu$g/kg/day to 100 mg/kg/day of patient body weight, although, as noted above, this will be subject to therapeutic discretion. More preferably, this dose is at least 0.1 mg/kg/day, and most preferably for humans between about 0.1 and 10 mg/kg/day.

If given continuously, the compound of the present invention is typically administered parenterally at a dose rate of about 100 $\mu$g/kg/hour to about 500 $\mu$g/kg/hour, either by 1–4 injections per day or by continuous subcutaneous infusions, for example, using a mini-pump. An intravenous bag solution may also be employed. The key factor in selecting an appropriate dose is the result obtained, as measured by increases in insulin-like activity in the patient. The length of treatment needed to observe changes and the interval following treatment for responses to occur appears to vary depending on the desired effect.

Pharmaceutical compositions containing the compounds of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a nontoxic solid, semisolid or liquid filler, diluent, encapsulating material or formulation auxiliary of any type. The term "parenteral" as used herein refers to modes of administration which include intravenous, intramuscular, intraperitoneal, intrastermal, subcutaneous and intraarticular injection and infusion.

The compounds of the present invention are also suitably administered by sustained-release systems. Suitable examples of sustained-release compositions include semipermeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman et al., *Biopolymers* 22:547–556 (1983)), poly (2-hydroxyethyl methacrylate) (Langer et al., *J Biomed. Mater. Res.* 15:167–277 (1981), and Langer, *Chem. Tech.* 12:98–105 (1982)), ethylene vinyl acetate (Langer et al.) or poly-D-(–)-3-hydroxybutyric acid (EP 133,988). Sustained-release compositions also include liposomally entrapped compounds. Liposomes containing one or more of the compounds of the present invention may be prepared by methods known per se: DE 3,218,121; Epstein et al., *Proc. Natl. Acad. Sci. (USA)* 82:3688–3692 (1985); Hwang etal., *Proc. Natl. Acad. Sci. (USA)* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy.

For parenteral administration, in one embodiment, the compound of the present invention is formulated generally by mixing it at the desired degree of purity, in a unit dosage injectable form (solution, suspension, or emulsion), with a pharmaceutically acceptable carrier, i.e., one that is nontoxic to recipients at the dosages and concentrations employed and is compatible with other ingredients of the formulation. For example, the formulation preferably does not include oxidizing agents and other compounds that are known to be deleterious to carbohydrates.

Generally, the formulations are prepared by contacting the compound of the present invention uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The compound of the present invention is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers may result in the formation of salts depending upon the particular substitutent(s) on the disaccharide.

The compound of the present invention ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous disaccharide solution, and the resulting mixture is lyophilized. The infusion solution is prepared by reconstituting the lyophilized disaccharide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLES

I. Prepartation of 4'-O-(2-Deoxy-2-Amino-β-D-Galactopyranosyl)-D-Chiro-Inositol

A detailed procedure for preparing this compound is as follows.

A. Preparation of 1',2';5',6'-Di-O-Isopropylidene-3-O-(Trimethylsilyethoxymethyl)-D-Chiro-Inositol.

1,2;5,6-Di-O-isopropylidene-D-chiro-inositol (942 mg), 0.83 ml of trimethylsilylethoxymethyl chloride (SEM-Cl) and 1.9 ml of diisopropylethyl amine (DIPEA) were dissolved in 20 ml of dry methylene chloride and refluxed for 16 hours. The solution was concentrated in vacuo and the last traces of volatile material were removed under high vacuum (500 m Torr) for four days to yield pure product. The yield was 1.04 g (73%).

B. Prepartation of 2-DEOXY-2-Dinitrophenylamino D-Galactose.

Galactosamine hydrochloride (10 g) was stirred with 20 ml of distilled acetone and 50 ml of deionized water. 2,4-Dinitrofluorobenzene (5.8 ml) was added followed by 4.9 g of sodium carbonate. The mixture was stirred at room temperature for 18 hours when a yellow precipitate was formed. The material was suction filtered to dryness, dissolved in 30 ml of dry methanol. Benzene (120 ml) was added followed by enough hexane to make the solution slightly cloudy (approximately 50 ml) at which time the cloudy suspension was seeded to produce 5.6 g (35%) of the product.

An alternate procedure was used to concentrate the mixture after 18 hours reaction time and load the crude material on a 3×20 cm flash column packed with silica gel 60 and elute the column with chloroform:isopropanol (3:1) and removing the solvent in vacuo to dryness. From 6 g of galactosamine hydrochloride, 3.48 ml of dinitrofluorobenzene, 2.94 g of sodium carbonate, 30 ml of water and 120 ml of acetone, 7.37 g (77%) of the product was obtained.

C. Preparation of 1-Bromo-1,2-Didexoy-2-Dinitrophenyl-3,4,6-Tri-O-Acetyl-D-Galactose.

2-Deoxy-2-dinitrophenylamino galactose (7.37 g) was dissolved in 50 ml of dry pyridine and the solution was cooled to 0° C. Acetic anhydride (50 ml) was added and the solution stirred for ten hours while allowing to warm to 10–15° C.

The solution was poured into 500 ml of ice water and the mixture was suction filtered. The precipitate was recrystallized from 500 ml hot 95% ethanol to yield 11.06 g (100%) of the product.

1,3,4,6-Tetra-O-acetyl-2-deoxy-2-dinitrophenylamino-galactose (6.83 g) was moistened with 12 ml of dry chloroform and cooled to 0° C. where 100 ml of 30% hydrogen bromide in acetic acid was added dropwise and the solution was stirred for two hours after the addition was complete. The solution was poured into 350 ml of ice water and extracted with 4×100 ml of chloroform. The combined chloroform extracts were washed with 2×100 ml saturated aqueous sodium bicarbonate, 100 ml of water, dried over magnesium sulfate, filtered and concentrated in vacuo. After 25 hours of drying under high vacuum, 7.08 g (99%) of the product was obtained.

D. Glycosylation Procedure to Prepare 4'-O-[3,4,6-Tri-O-Acetyl-2-Deoxy-2-Dinitrophenylamino-β-D-Galactopyranosyl]-3'-O-Trimethyl-Silyethoxymethyl-1',2'; 5',6'-Di-O-Isopropylidene-D-Chiro-Inositol.

Vacuum dried 1-bromo-1,2-dideoxy-3,4,6-tri-O-acetyl-2-dinitrophenylamino-D-galactose (170 mg) and 1,2;5,6-di-0-isopropylidene-3-O-(trimethylsilylethoxymethyl)-D-chiro-inositol (100 mg) were dissolved in 10 ml of dry methylene chloride and the solution stirred at room temperature. Under a nitrogen shroud, 500 mg of freshly activated 4 angstrom powdered molecular sieves was added and stirred for one hour. At that time 0.04 ml of tetramethyl urea and 82 mg of silver triflate were added under a nitrogen shroud. The heterogeneous mixture was stirred at room temperature for 21 hours where three drops of triethylamine was added; the mixture was filtered and the solvents removed in vacuo. The crude material was loaded on a 2×25 cm flash column packed with silica gel 60 and the column was eluted with 790 ml of 4:1 petroleum ether:ethyl acetate and 100 ml of 2:1 petroleum ether:ethyl acetate to isolate 90 mg. of the isomer (23%) and 42 mg of the beta-isomer (19%)

E. Preparation of 4'-O-[2-Deoxy-2-Amino-β-D-Galactopyranosyl]-3'-O-Trimethylsilylethoxymethyl-1',2'; 5',6'-Di-O-Isopropylidene-D-Chiro-Inositol 4'-O-[3,4,6-Tri-O-acetyl-2-deoxy-2-dinitrophenylamino-β-D-galactopyranosyl]-3'-O-trimethylsilylethoxymethyl-1', 2';5',6'-di-O-isopropylidene-D-chiro-inositol (37.5 mg) was stirred with 3.5 ml of 1 M aqueous lithium hydroxide and 7 ml of dioxan and heated to 90° C. for 28 hours. Acetic acid (4 ml) was added to pH S and the solvents were removed in vacuo. The residue was dissolved in methanol, 1 g of silica gel 60 was added and the methanol was removed in vacuo. The preabsorbed material was loaded on a 1×15 cm flash column packed with silica gel 60 and the column was eluted with 3:1 chloroform:isopropanol to isolate 22.1 mg of the product (90%).

F. Prepartation of 4'-O-[2-Deoxy-2-Amino-β-D-Galactopyranosyl]-D-Chiro-Inositol

4'-O-[2-Deoxy-2-amino-beta-D-galactopyranosyl]-3'-O-trimethylsilylethoxymethyl- 1',2'; 5',6'-di-O-isopropylidene-D-chiro-inositol (124 mg) was dissolved in 10 ml of 80% acetic acid and the solution heated to 75° C. for 18 hours. The solvents were removed in vacuo to yield 76 mg (99%)

of the product. The product was further purified using HPLC with a $C_{18}$ stationary phase and a water eluant.

II. Preparation of 4'-O-(2-Deoxy-2-Amino-β-D-Galactopyranosyl-D-Pinitol

A detailed description of the synthetic pathway by which this compound is prepared is as follows.

A. Preparation of 4'-O-[2-Deoxy-2-Dinitrophenylamino-3,4,6-Tri-O-Acetyl-β-D-Galactopyranosyl]-1',2';5',6'-Di-O-Isopropylidene-D-Pinitol Vacuum dried 1-bromo-1,2-dideoxy-3,4,6-tri-O-acetyl-2-dinitrophenylamino-galactose (3.9 g) and 1 g of 1,2;5,6-di-O-isopropylidene-D-pinitol were dissolved in 100 ml of dry methylene chloride and the solution stirred at room temperature. Under a nitrogen shroud, freshly activated 4 angstrom powdered molecular sieves was added and the mixture stirred for one hour. At that time 0.87 ml of tetramethyl urea and 1.86 of vacuum dried silver triflate was added under a nitrogen shroud and the mixture stirred at 0° C. for 18 hours. The mixture was filtered and the filtrate was dried in vacuo. The crude oil was loaded on a 5×20 cm flash column packed with silica gel 60 and the column was eluted with 2:1 petroleum ether:ethyl acetate to yield 2.108 g (76%) of the beta anomer.

B. Preparation of 4'-O-[2-Deoxy-2-Amino-β-D-Galactopyranosyl]-1',2'; 5',6'-Di-O-Isopropylidene-D-Pinitol 4'-O-[3,4,6-Tri-O-acetyl-2-deoxy-2-dinitrophenylamino-β-D-galactopyranosyl]-1',2';5',6'-di-O-isopropylidene-D-pinitol (902.1 mg) was stirred with 3.5 ml of 1 M aqueous lithium hydroxide and 7 ml dioxan and heated to 95° C. for 72 hours. Acetic acid (2 ml) was added and the solvents were removed in vacuo. The crude material was loaded on a 2×10 cm flash column packed with silica gel 60 and eluted with 3:1 chloroform:isopropanol to yield 361 mg (610–.) of the product, which was recrystallized from isopropanol to yield 74 mg of crystalline product.

C. Preparation of 4'-O-(2-Deoxy-2-Amino-β-D-Galactopyranosyl)-D-Pinitol

4'-O-[2-Deoxy-2-amino-β-D-galactopyranosyl]-1',2';5', 6'-di-O-isopropylidene-D-pinitol (101 mg) was dissolved in 5 ml of 80% acetic acid and the solution heated to 750° C. for 24 hours. The solvents were removed in vacuo. The residue was passed through a C-18 Millipore cartridge and eluted with acetonitrile. The residue (which weighed 64 mg) was recrystallized from isopropanol to yield 25 mg of the product.

III. Reduction of Elevated Blood Glucose Concentration

These compounds are useful in the treatment of defects in glucose metabolism, such as impaired glucose tolerance, elevated blood sugar associated with type II diabetes, and insulin resistance and the physiological conditions associated therewith.

For example, rats were injected intravenously with 70 mg/kg of streptozotocin. After ten days, when resultant hyperglycemia was established, the animals were anesthetized with ketamine and zero time blood glucose levels were established by way of tail vein sampling. An experimental group was given 2 mg/kg 4'-O-(2-deoxy-2-amino-β-D-galactopyranosyl)-D-pinitol by intravenous injection via the tail vein, and a control group was given an equal volume of saline. Blood glucose levels were measured over time in both groups. All measurements were made while the subjects were under ketamine anesthesia. Evaluation of the time course data by two-way analysis of variance indicated a significant overall effect of the disaccharide to lower blood glucose concentration (p<0.01). Thirty minutes after administration of the disaccharide, blood glucose levels were decreased from pretreatment concentration by 30% (+/−9.5) in the experimental group, while levels in the control group decreased only 2.5% (+/−2.6).

What is claimed is:

1. A compound of the formula (I)

wherein $R_1$–$R_2$ are each independently selected from the group consisting of:
(a) a hydrogen atom; and
b) a lower alkyl group, straight or branched chain, having 1 to 8 carbon atoms; or $R_1$–$R_2$ and the nitrogen atom to which they are bonded may together form a heterocyclic group;

$R_3$–$R_{10}$ are each independently selected from the group consisting of:
(a) a hydrogen atom;
(b) an alkyl group, straight or branched chain, having 1 to 24 carbon atoms;
(c) a cycloalkyl group having 3 to 10 carbon atoms;
(d) an alkenyl group, straight or branched chain, having 2 to 24 carbon atoms;
(e) a cycloalkenyl group having 4 to 10 carbon atoms and one or more non-adjacent double bonds;
(f) an aryl group having 6 to 10 carbon atoms;
(g) an aralkyl group having 7 to 34 carbons atoms;
(h) a heteroaryl group having 4 to 9 carbon atoms and at least one heteroatom selected from the group consisting of oxygen, nitrogen and sulfur;
(i) a carboxyalkyl group, straight or branched chain, having 2 to 24 carbon atoms;
(j) a carboxyaryl group having 7 to 34 carbon atoms; and
(k) a heterocyclic group having 2 to 9 carbon atoms and at least one heteroatom selected from the group consisting of oxygen, sulfur and nitrogen; or any adjacent two of $R_3$–$R_{10}$ may together form a cycloalkyl group or heterocyclic group;

and $X_1$ and $X_2$ are each independently selected from the group consisting of an oxygen atom, a sulfur atom and a nitrogen atom.

2. The compound of claim 1, wherein $X_1$ and $X_2$ are each an oxygen atom.

3. The compound of claim 1, wherein said compound has the formula (II)

(II)

4. The compound of claim 3, wherein at least one of $R_6$–$R_{10}$ is an alkyl group.

5. The compound of claim 4, wherein $R_8$ is an alkyl group.

6. The compound of claim 4, wherein $R_8$ is a methyl group.

7. The compound of claim 2, wherein the 2-amino-D-hexosamine is selected from the group consisting of 2-amino-D-glucosamine and 2-amino-D-galactosamine.

8. The compound of claim 7, wherein said 2-amino-D-hexosamine is 2-amino-D-galactosamine.

9. The compound of claim 1, wherein at least one of $R_3$–$R_{10}$ is selected from the group consisting of an alkyl group, a cycloalkyl group, an aryl group, an aralkyl group, a carboxyalkyl group, and a carboxyaryl group.

10. The compound of claim 1, wherein $R_1$ and $R_2$ are each a hydrogen atom.

11. The compound of claim 2, wherein $R_1$ and $R_2$ are each a hydrogen atom.

12. The compound of claim 3, wherein $R_1$ and $R_2$ are each a hydrogen atom.

13. A pharmaceutical composition comprising:
   (i) an effective amount of a compound of the formula (I)

(I)

wherein
   $R_1$–$R_2$ are each independently selected from the group consisting of:
   (a) a hydrogen atom; and
   (b) a lower alkyl group, straight or branched chain, having 1 to 8 carbon atoms; or
   $R_1$–$R_2$ and the nitrogen atom to which they are bonded may together form a heterocyclic group;
   $R_3$–$R_{10}$ are each independently selected from the group consisting of:
   (a) a hydrogen atom;
   (b) an alkyl group, straight or branched chain, having 1 to 24 carbon atoms;
   (c) a cycloalkyl group having 3 to 10 carbon atoms;
   (d) an alkenyl group, straight or branched chain, having 2 to 24 carbon atoms;
   (e) a cycloalkenyl group having 4 to 10 carbon atoms and one or more non-adjacent double bonds;
   (f) an aryl group having 6 to 10 carbon atoms;
   (g) an aralkyl group having 7 to 34 carbons atoms;
   (h) a heteroaryl group having 4 to 9 carbon atoms and at least one heteroatom selected from the group consisting of oxygen, nitrogen and sulfur;
   (i) a carboxyalkyl group, straight or branched chain, having 2 to 24 carbon atoms;
   (j) a carboxyaryl group having 7 to 34 carbon atoms; and
   (k) a heterocyclic group having 2 to 9 carbon atoms and at least one heteroatom selected from the group consisting of oxygen, sulfur and nitrogen; or
   any adjacent two of $R_3$–$R_{10}$ may together form a cycloalkyl group or heterocyclic group;
and
   $X_1$ and $X_2$ are each independently selected from the group consisting of an oxygen atom, a sulfur atom and a nitrogen atom; and
   (ii) a pharmaceutically acceptable carrier.

14. The composition of claim 13, wherein $X_1$ and $X_2$ are each an oxygen atom.

15. The composition of claim 13, wherein said compound has the formula (II)

(II)

16. The composition of claim 15, wherein at least one of $R_6$–$R_{10}$ is an alkyl group.

17. The composition of claim 16, wherein $R_8$ is an alkyl group.

18. The composition of claim 16, wherein $R_8$ is a methyl group.

19. The composition of claim 14, wherein the 2-amino-D-hexosamine is selected from the group consisting of 2-amino-D-glucosamine and 2-amino-D-galactosamine.

20. The composition of claim 19, wherein said 2-amino-D-hexosamine is 2-amino-D-galactosamine.

* * * * *